US 8,574,238 B2

(12) United States Patent
Zannis et al.

(10) Patent No.: US 8,574,238 B2
(45) Date of Patent: Nov. 5, 2013

(54) INSTRUMENTS, KIT AND METHOD FOR SUTURE MANAGEMENT

(75) Inventors: Anthony D. Zannis, Fort Wayne, IN (US); Prasanna Malaviya, Fort Wayne, IN (US); Keith M. McGrath, Warsaw, IN (US); Herbert E. Schwartz, Fort Wayne, IN (US)

(73) Assignee: DePuy Mitek, LLC, Raynham, MA (US)

( * ) Notice: Subject to any disclaimer, the term of this patent is extended or adjusted under 35 U.S.C. 154(b) by 1792 days.

(21) Appl. No.: 11/261,840

(22) Filed: Oct. 28, 2005

(65) Prior Publication Data
US 2006/0095054 A1    May 4, 2006

Related U.S. Application Data

(60) Provisional application No. 60/623,365, filed on Oct. 29, 2004.

(51) Int. Cl.
*A61B 17/58* (2006.01)
*A61B 17/60* (2006.01)
*A61F 2/00* (2006.01)

(52) U.S. Cl.
USPC ............................................................. 606/99

(58) Field of Classification Search
USPC ............... 606/108, 72, 75, 99, 300–321, 232, 606/139–150; 128/784, 4, 214, 347, 419; 623/1.42
See application file for complete search history.

(56) References Cited

U.S. PATENT DOCUMENTS

| | | | |
|---|---|---|---|
| 4,243,050 A * | 1/1981 | Littleford ...................... 607/122 |
| 4,880,429 A | 11/1989 | Stone | |
| 4,888,000 A * | 12/1989 | McQuilkin et al. ...... 604/164.05 |
| 5,007,934 A | 4/1991 | Stone | |
| 5,009,643 A * | 4/1991 | Reich et al. .............. 604/165.02 |
| 5,108,438 A | 4/1992 | Stone | |
| 5,199,561 A | 4/1993 | Roshdy et al. | |
| 5,211,656 A * | 5/1993 | Maddocks et al. ............ 606/236 |
| 5,306,311 A | 4/1994 | Stone et al. | |
| 5,318,542 A | 6/1994 | Hirsch et al. | |
| 5,429,117 A | 7/1995 | McNamara et al. | |
| 5,649,939 A | 7/1997 | Reddick | |
| 5,681,353 A | 10/1997 | Li et al. | |
| 5,735,903 A | 4/1998 | Li et al. | |
| 5,797,929 A | 8/1998 | Andreas | |
| 5,948,002 A * | 9/1999 | Bonutti ......................... 606/232 |
| 6,027,480 A | 2/2000 | Davis et al. | |
| 6,042,610 A | 3/2000 | Li et al. | |

(Continued)

FOREIGN PATENT DOCUMENTS

DE    33 47 150 A    7/1985

*Primary Examiner* — Sameh Boles

(57) ABSTRACT

A cannula has a flange and a body with slots extending through the entire flange and into the body. The cannula may also have a longitudinal slot extending its entire length. An obturator used with the cannula may also have a longitudinal slot extending along its length. A surgical method using these instruments includes separating lengths of suture and managing the suture by placing lengths of suture in the slots in the cannula. The cannula and obturator may be used after suture is already in place by placing the suture in the longitudinal slots and then introducing the cannula and obturator to the tissue defect site. The cannula may also be used to deliver a therapeutic implant to the tissue defect site. The instruments and method may be used in mensical surgery.

10 Claims, 6 Drawing Sheets

(56) References Cited

U.S. PATENT DOCUMENTS

| | | | |
|---|---|---|---|
| 6,099,506 A | 8/2000 | Macoviak et al. | |
| 6,273,871 B1 | 8/2001 | Davis et al. | |
| 6,416,469 B1 | 7/2002 | Phung et al. | |
| 6,450,951 B2 | 9/2002 | Phung et al. | |
| 6,491,714 B1 * | 12/2002 | Bennett | 606/232 |
| 6,558,354 B1 | 5/2003 | Howell | |
| 7,326,194 B2 * | 2/2008 | Zinger et al. | 604/410 |
| 7,473,259 B2 | 1/2009 | Jacobs et al. | |
| 2001/0056283 A1 * | 12/2001 | Carter et al. | 606/148 |
| 2002/0193830 A1 | 12/2002 | Bonutti | |
| 2003/0009177 A1 * | 1/2003 | Middleman et al. | 606/127 |
| 2003/0021827 A1 | 1/2003 | Malaviya et al. | |
| 2003/0023316 A1 | 1/2003 | Brown et al. | |
| 2003/0032961 A1 * | 2/2003 | Pelo et al. | 606/72 |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0044444 A1 | 3/2003 | Malaviya et al. | |
| 2003/0049299 A1 | 3/2003 | Malaviya et al. | |
| 2003/0078617 A1 | 4/2003 | Schwartz et al. | |
| 2003/0181800 A1 | 9/2003 | Bonutti | |
| 2004/0267276 A1 | 12/2004 | Camino et al. | |
| 2004/0267277 A1 | 12/2004 | Zannis et al. | |
| 2004/0267304 A1 | 12/2004 | Zannis et al. | |
| 2006/0095048 A1 | 5/2006 | Zannis et al. | |
| 2006/0095049 A1 | 5/2006 | Zannis et al. | |
| 2006/0095053 A1 | 5/2006 | Zannis et al. | |
| 2006/0095054 A1 | 5/2006 | Zannis | |
| 2006/0211953 A1 | 9/2006 | Zannis et al. | |
| 2007/0185568 A1 * | 8/2007 | Schwartz | 623/1.42 |
| 2007/0276288 A1 * | 11/2007 | Khaw | 600/566 |
| 2008/0065120 A1 | 3/2008 | Zannis et al. | |

* cited by examiner

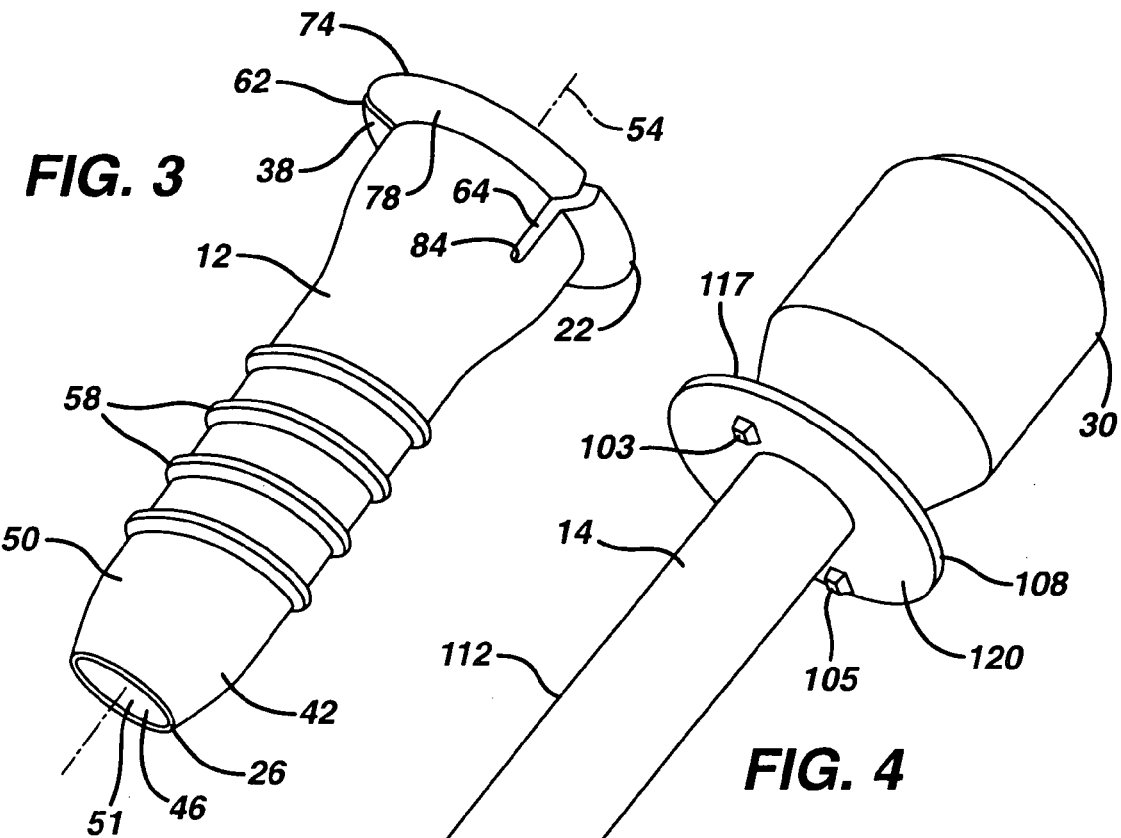
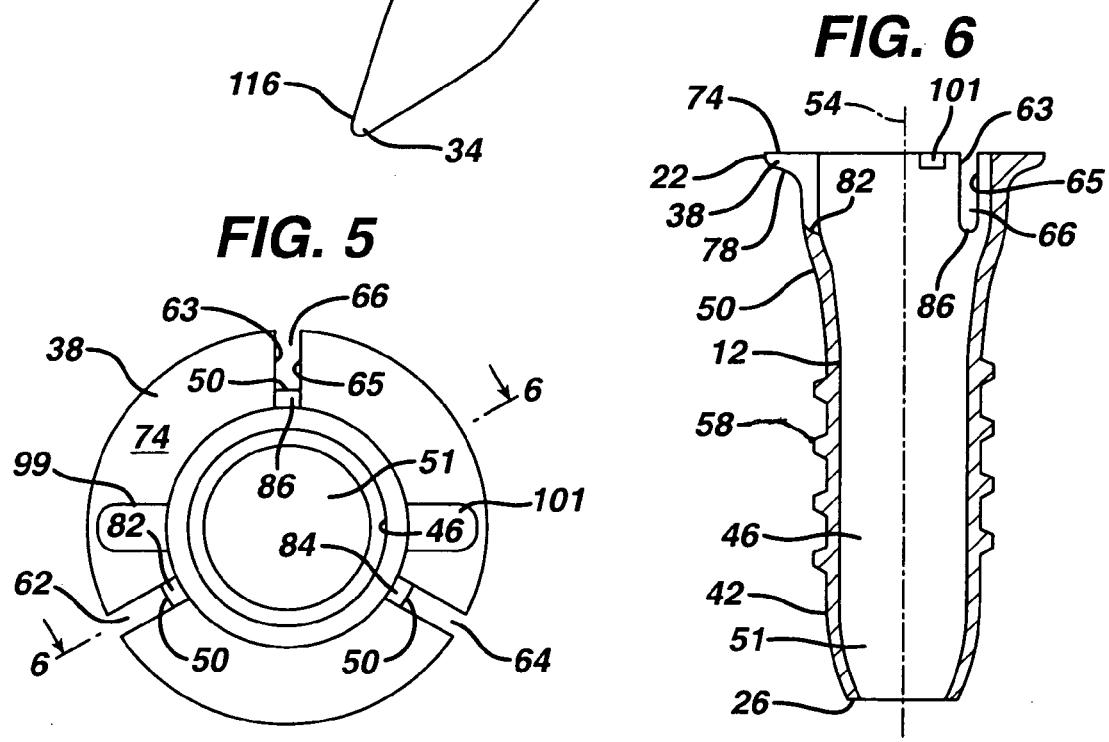

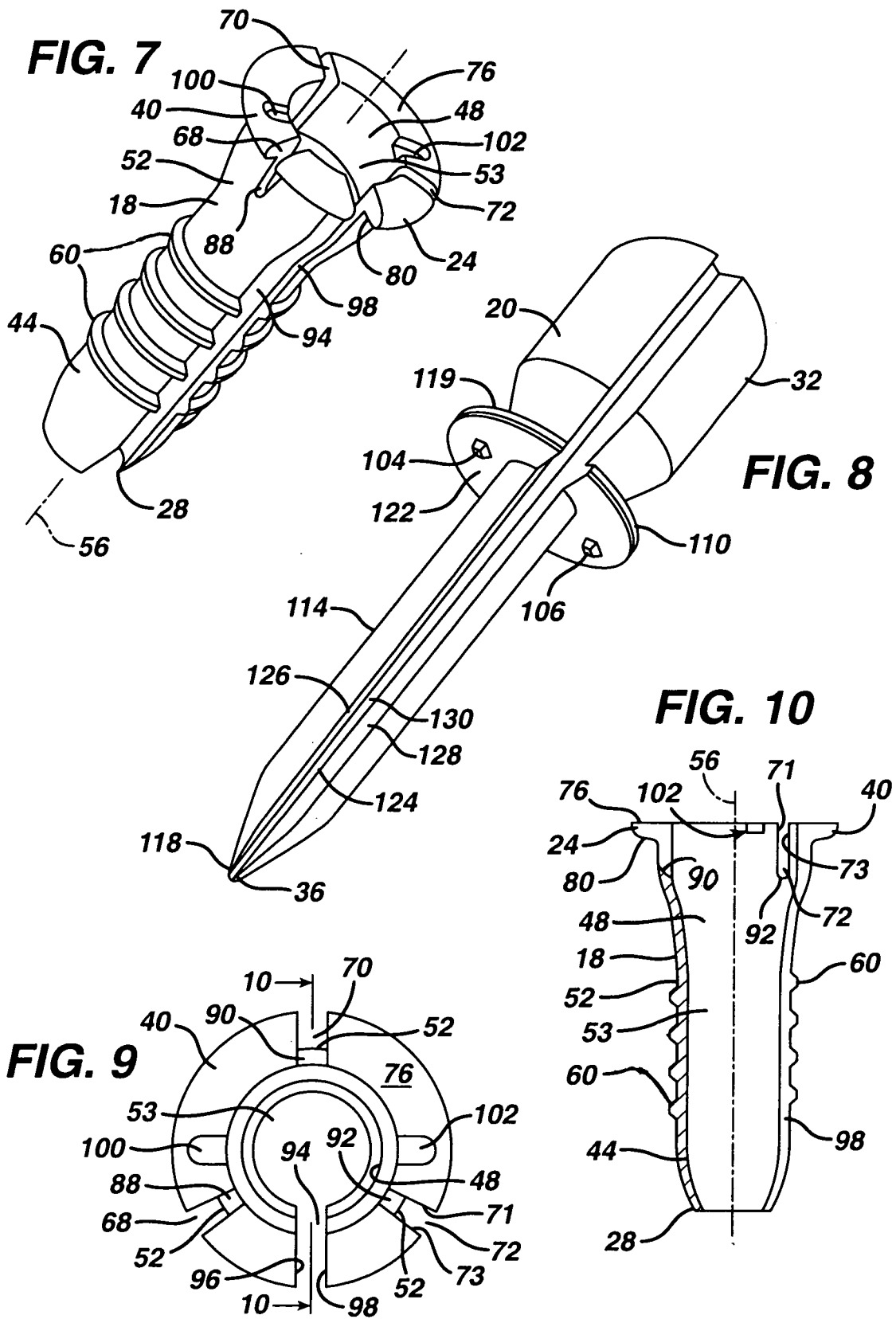

INSTRUMENTS, KIT AND METHOD FOR SUTURE MANAGEMENT

This application claims the benefit of U.S. Provisional Application No. 60/623,365, filed on Oct. 29, 2004, by Anthony Zannis, Keith McGrath, Prasanna Malaviya, Herbert Schwartz, and entitled "Instruments, Kit and Method for Suture Management," which is incorporated by reference herein in its entirety.

FIELD OF THE INVENTION

The present invention relates to surgical instruments and more particularly to cannulae and obturators that can be used to manage suture during surgery.

BACKGROUND OF THE INVENTION

The meniscus is a crescent-shaped disc of cartilage tissue located between the femoral condyles and the tibial plateau. The meniscus functions as a shock absorber, absorbing the compressive and shear forces in the knee joint. Since the meniscus is aneural, the load-bearing function occurs in a painless fashion in a healthy knee joint. The meniscus also provides a low-friction surface for articulation within the knee joint.

The meniscus is frequently damaged in twisting injuries or with repetitive impact over time. Meniscus degeneration also can occur by aging: as a person ages, the meniscus becomes soft in the middle and even common motions such as squatting can cause meniscal tears.

Surgical procedures for treating meniscal damage can be broadly classified as either tear repairs or menisectomies. A tear repair is most commonly performed when the tear is a clean longitudinal vertical lesion in the vascular red-red zone of the meniscus. The basic strategy is to stabilize the tear by limiting or eliminating radial separation of the faces of the tear when the meniscus is load bearing. Devices for use in meniscal tear repair are available on the market, including, for example, the RAPIDLOC Meniscal Repair System available from DePuy Mitek of Westwood, Mass. and Somerville, N.J.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint.

A variety of orthopaedic implants are available for treating damaged soft tissue. Orthopaedic implants for treatment of damaged menisci are disclosed in the following U.S. Pat. Nos. 6,042,610; 5,735,903; 5,681,353; 5,306,311; 5,108,438; 5,007,934; and 4,880,429.

Tear repairs and menisectomies are commonly performed arthroscopically. In arthroscopy, small incisions are made at the affected joint to form portals for the insertion of instruments, including a small lens and lighting system (an arthroscope). The arthroscope is connected to a viewing device, such as a television camera to allow the surgeon to see the interior of the joint. Other instruments are inserted through other portals to perform a variety of tasks. For example, the surgical instrument may include an implement for manipulating the native meniscal tissue (for example, tissue grasping, tissue cutting, bone abrading), or an implement for introducing and implanting a therapeutic implant.

While arthroscopic instruments, such as cannulae and obturators or trocars have been available for use in tear repairs and menisectomies, there remains a need for a device that can be used to deliver a therapeutic implant to the tissue defect site and to manage the sutures used in fixating the therapeutic device to the native meniscus.

SUMMARY OF THE INVENTION

The present invention provides an instrument set and a surgical technique for delivering a therapeutic implant to a tissue defect site and to managing sutures used in fixating the therapeutic implant to the tissue.

In one aspect, the present invention provides a surgical cannula having a proximal end, a distal end and a central longitudinal axis. The cannula comprises an annular flange at the proximal end and a body extending from the annular flange to the distal end of the cannula. The flange has a central opening, a top surface and a bottom surface. The body includes a proximal portion adjacent to the annular flange and an interior surface defining a central axial channel extending from the central opening of the annular flange to the distal end. The body is open at the distal end. The body also includes an exterior surface; a portion of the exterior surface between the annular flange and the distal end has threads. A pair of spaced surfaces define a through slot extending radially across the entire flange and through the entire thickness of the flange. The through slot further extends distally through the proximal portion of the body from the exterior surface to the interior surface. The through slot terminates at a location distal to the bottom surface of the annular flange and proximal to the distal end of the cannula.

In another aspect, the present invention provides a surgical cannula kit comprising a cannula and an obturator. The cannula includes a proximal end, a distal end and a central longitudinal axis. The cannula also includes an annular flange at the proximal end. The flange has a central opening, a top surface and a bottom surface. The cannula also includes a body extending from the annular flange to the distal end of the cannula. The body includes a proximal portion adjacent to the annular flange and an interior surface defining a central axial channel extending from the central opening of the annular flange to the distal end. The body is open at the distal end. The body further includes an exterior surface. The cannula further comprises a pair of spaced surfaces defining a longitudinal slot extending through the flange and body of the cannula from the proximal end to the distal end. The longitudinal slot provides a passageway between the longitudinal channel of the cannula and the exterior of the cannula along the entire length of the cannula. The obturator includes a proximal portion, a distal portion terminating in a distal end, an intermediate portion and a flange between the intermediate portion and the proximal portion. The obturator is sized and shaped so that the intermediate portion is receivable and slidable in the central axial channel of the cannula. The obturator further comprises a pair of spaced surfaces defining a longitudinal slot in the distal portion, intermediate portion, flange and proximal portion of the obturator.

In another aspect, the present invention provides a method of delivering a therapeutic implant to a tissue defect site within a joint space of a patient. The method comprises providing a cannula, an obturator and an implant. The cannula includes a proximal end, a distal end and a central longitudinal axis. The cannula has an annular flange at the proximal end. The flange has a central opening, a top surface and a bottom surface. The cannula also has a body extending from the annular flange to the distal end of the cannula. The body includes a proximal portion adjacent to the annular flange and an interior surface defining a central axial channel extending from the central opening of the annular flange to the distal end. The body is open at the distal end. The body further includes an exterior surface. The cannula also includes a pair of spaced surfaces defining a longitudinal slot extending through the flange and body of the cannula from the proximal end to the distal end. The longitudinal slot provides a passageway between the longitudinal channel of the cannula and the exterior of the cannula along the entire length of the cannula. The obturator includes a proximal portion, a distal portion terminating in a distal end, an intermediate portion and a flange between the intermediate portion and the proximal portion. The obturator is sized and shaped so that the intermediate portion is receivable and slidable in the central axial channel of the cannula. The obturator further includes a pair of spaced surfaces defining a longitudinal slot in the distal portion, intermediate portion, flange and proximal portion. The method further includes creating an insertion incision in the patient. Suture is passed through the therapeutic implant while the implant is outside of the joint space. The suture is then passed through tissue within the joint space so that a portion of the suture is within the joint space and a portion of the suture is outside of the joint space. The cannula and obturator are assembled so that the distal tip of the obturator is exposed past the distal end of the cannula. The portion of the suture outside of the joint space is moved through the longitudinal slot of the cannula and into the longitudinal slot of the obturator. The assembled cannula and obturator is inserted into the insertion incision with a portion of the suture in the longitudinal slot of the obturator. The assembled cannula and obturator are moved to the tissue defect site within the joint space with a portion of the suture in the longitudinal slot of the obturator. The obturator is retraced. The implant is moved through the cannula to the defect site and fixed at the defect site.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 3 is a perspective view of the cannula of the instrument set or assembly of FIG. 1;

FIG. 4 is a perspective view of the obturator of the instrument set or assembly of FIG. 1;

FIG. 5 is a top end view of the cannula of FIGS. 1 and 3;

FIG. 6 is a cross-section of the cannula of FIGS. 1, 3 and 5, taken along line 6-6 of FIG. 5;

FIG. 7 is a perspective view of the cannula of the instrument set of FIG. 2;

FIG. 8 is a perspective view of the obturator of the instrument set of FIG. 2;

FIG. 9 is a top end view of the cannula of FIGS. 2 and 7;

FIG. 10 is a cross-section of the cannula of FIGS. 2, 7 and 9, taken along line 10-10 of FIG. 9;

DETAILED DESCRIPTION

Figure 1:
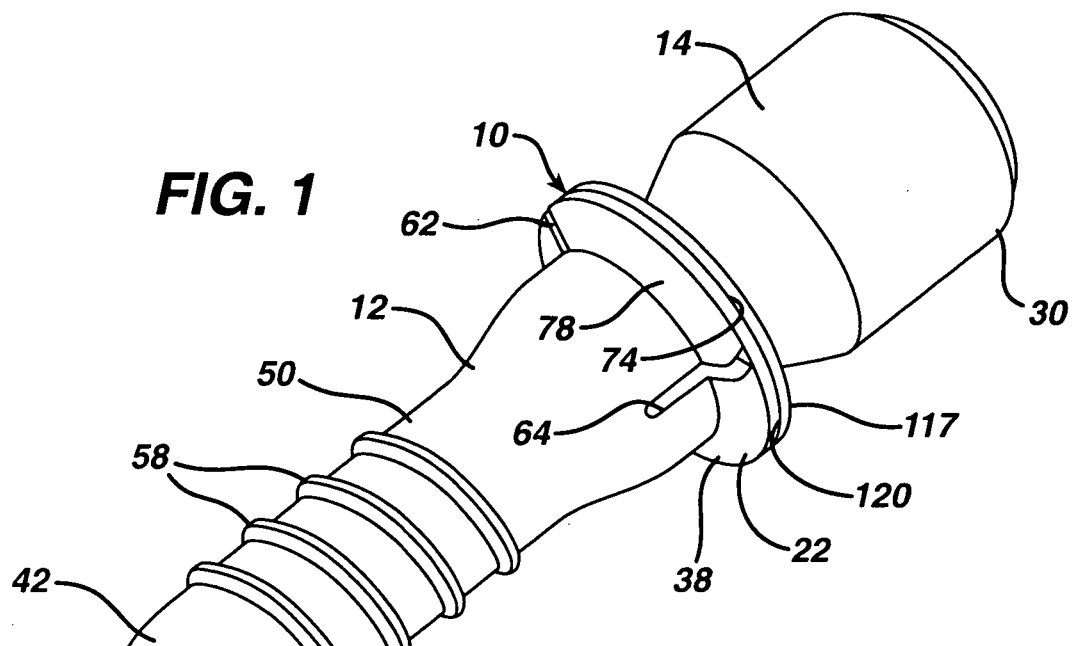
FIG. 1 is a perspective view of a first embodiment of a set or assembly of surgical instruments incorporating the principles of the present invention.
Figure 2:
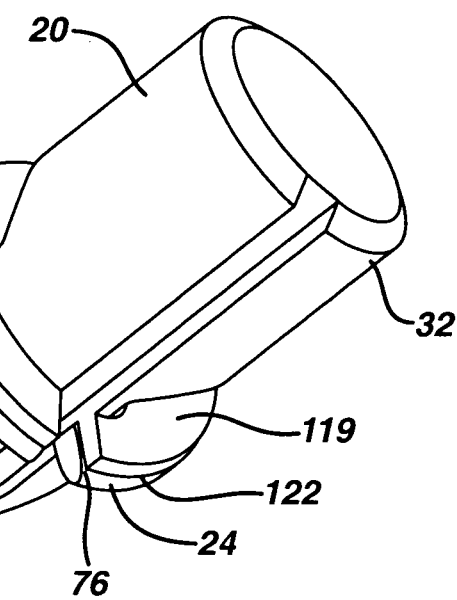
FIG. 2 is a perspective view of a second embodiment of a set or assembly of surgical instruments embodying the principles of the present invention.

Surgical instruments embodying the principles of the present invention are illustrated in the accompanying drawings. FIG. 1 illustrates a first embodiment of a surgical instrument set or assembly 10 comprising a cannula 12 and an obturator 14. FIG. 2 illustrates a second embodiment of a surgical instrument set or assembly 16 comprising a cannula 18 and an obturator 20.

Both of the illustrated sets or assemblies of instruments 10, 16 are useful in delivering therapeutic implants to tissue defect sites and in managing fixation of the therapeutic implants. As used herein, "defect" is intended to include both tissue tears and gaps in tissue left after part of the tissue has been removed, such as through a menisectomy.

Each cannula 12, 18 includes a proximal portion 22, 24 and a distal portion 26, 28. Each obturator 14, 20 also includes a proximal portion 30, 32 and a distal portion 34, 36. As used herein, "proximal" refers to the end or portion nearer to the surgeon, and "distal" refers to the end or portion further from the surgeon.

Each cannula 12, 18 also includes a proximal annular flange 38, 40 and a body 42, 44 with an interior surface 46, 48 (shown in FIGS. 5 and 9) and an exterior surface 50, 52. Each interior surface 46, 48 defines a central axial channel 51, 53. Each cannula is open at its proximal and distal ends. As shown in FIGS. 3, 6, 7 and 10, at the proximal end of the tubular body 42, 44, the cannula flares outwardly away from the central longitudinal axis 54, 56. At the distal end of the tubular body 42, 44, the body tapers toward the central longitudinal axis 54, 56. Between the proximal flared portion and distal tapered portion, the intermediate portion of each body 42, 44 is substantially cylindrical. Helical threads 58, 60 are on the exterior surface of the intermediate portion of the body. Each thread has a substantially flat outermost surface and angled side walls.

Each cannula 12, 18 also includes a plurality of through slots 62, 64, 66, 68, 70, 72 defined by spaced surfaces in the flange and proximal portion of the body 42, 44. Examples of such spaced surfaces are shown at 63, 65 in FIGS. 5-6 for through slot 66 and at 71, 73 in FIGS. 9-10 for through slot 72; it should be understood that the spaced surfaces defining the other through slots are similar. As shown in FIGS. 5 and 9, each of the illustrated cannula has three through slots, spaced evenly about the annular end flange 38, 40. Each through slot 62, 64, 66, 68, 70, 72 extends radially through the entire flange 38, 40, from the top surface 74, 76 to the bottom surface 78, 80 and distally into the proximal portion of the body 42, 44 of the cannula 12, 18. Within the body of the cannula, each through slot 62, 64, 66, 68, 70, 72 extends across the entire thickness of the cannula, between the interior surface 46, 48 and exterior surface 50, 52. Each through slot 62, 64, 66, 68, 70, 72 has a distal end surface 82, 84, 86, 88, 90, 92 between the flange 38, 40 and the intermediate portion of the body 42, 44 carrying the threads 58, 60.

In the illustrated embodiments, the through slots 62, 64, 66, 68, 70, 72 have widths of 0.070 inches and lengths, from the top surfaces 74, 76 of the flanges 38, 40 to the distal end surfaces 82, 84, 86, 88, 90, 92 of 0.330 inches. It should be understood that these dimensions are provided as examples only; the present invention is not limited to any particular dimension unless expressly called for in the claims.

The cannula 18 of the second instrument set 16 has an additional feature not present in the cannula 12 of the first instrument set 10: the second illustrated cannula 18 has a longitudinal through slot 94 extending along its entire length, through the flange 40 and entire body 44. The longitudinal through slot 94 is defined by spaced surfaces 96, 98 as shown in FIG. 9 and provides a passageway between the central axial channel 53 and the area outside of the cannula 18 along the entire length of the cannula.

In addition, the top surface 74, 76 of each flange 38, 40 of each cannula 12, 18 has a pair of diametrically opposed radial indentations 99, 100, 101, 102. These radial indentations 99, 100, 101, 102 mate with pegs or projections 103, 104, 105, 106 on the obturator 14, 20 of the each instrument set 10, 16.

As previously identified, each obturator 14, 20 includes a distal portion 34, 36 and a proximal portion 30, 32. Each illustrated obturator also includes an annular flange 108, 110 adjacent the proximal portion 30, 32 and an intermediate portion 112, 114 between the annular flange 108, 110 and the distal portion 34, 36. In the illustrated embodiments, each distal portion 34, 36 terminates in a distal tip 116, 118. The distal tip 116, 118 may have a conical or frusto-conical shape. Each proximal portion 30, 32 serves as the obturator's handle, and to this end the outer surface of the proximal portion may be relieved with grooves or knurls to enhance gripping of the handle. The proximal end surface of each proximal portion 30, 32 may be rounded to permit a surgeon to comfortably push the obturator in a distal direction. The intermediate portion 112, 114 of each obturator 14, 20 may be substantially cylindrical.

Each obturator flange 108, 110 has a top surface 117, 119 and a bottom surface 120, 122. The bottom surface 120, 122 of each obturator flange 108, 110 carries the diametrically opposed pegs or projections 103, 104, 105, 106 that mate with the recesses 99, 100, 101, 102 in the top surfaces 74, 76 of each cannula flange 38, 40. When the each obturator 12, 16 is assembled with its respective cannula 12, 18, with the intermediate portion 112, 114 received within the longitudinal channel 51, 53 of its respective cannula 12, 18, as shown in FIGS. 1-2, 11 and 13, the bottom surface 120, 122 of the obturator flange 108, 110 is juxtaposed with the top surface 74, 76 of the cannula flange 38, 40 and the pegs 103, 104, 105, 106 are received in their mating recesses 99, 100, 101, 102 of the cannula flange 38, 40. With the pegs received in the recesses, relative rotation between each obturator 14, 20 and its cannula 12, 16 is limited or prevented. Thus, as the surgeon forces the assembly of the obturator and cannula through the patient's tissue, the surgeon can rotate the cannula 12, 16 by rotating the obturator 14, 20 so that the threads 58, 60 will set securely into the patient's tissue. It should be understood that the illustrated mating pegs and recesses are just one example of structures that can be used to prevent relative rotation between the cannula and its obturator when they are assembled; any structures that cooperate to prevent relative rotation between the obturator and cannula could be used, and the invention is not limited to any particular structure unless expressly called for in the claims.

Figure 15:
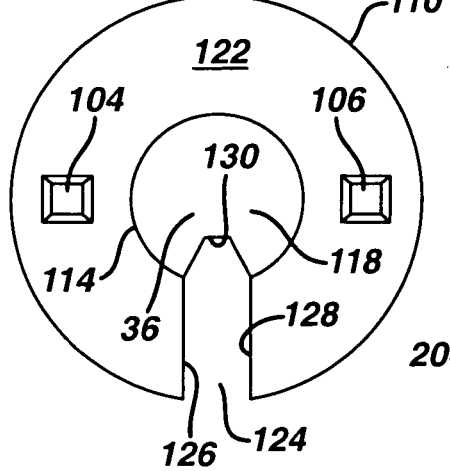
FIG. 15 is a distal end view of the obturator of FIGS. 2, 8 and 13.

The obturator of the second instrument set 16 has an additional feature not present in the obturator of the first instrument set 10: the second illustrated obturator 16 has a longitudinal slot 124 extending along its entire length, through the proximal handle portion 32, through the flange 110, through the intermediate portion 114 and through the entire distal portion 36, including the distal tip 118. The longitudinal slot 124 is defined by spaced surfaces 126, 128 and an axial surface 130 joining the two spaced surfaces 126, 128, as shown in FIGS. 8 and 15. When the second obturator 20 and second cannula 18 are assembled as in FIGS. 2 and 13, the longitudinal slot 124 of the obturator 20 is aligned with the longitudinal through slot 94 of the cannula 18, to provide a passageway from the exterior of the assembly through the longitudinal through slot 94 of the cannula 18 and into the longitudinal slot 124 of the obturator 20 along the entire length of the assembly.

The cannulae 12, 18 and obturators 14, 20 may be made of any suitable medical grade material for instruments, such as acetyl co-polymer. In the illustrated embodiments, the cannulae both have inner diameters ranging from 0.570 inches at the flared proximal end to 0.500 inches in the intermediate portion and to 0.415 inches at the distal end. The outer diameters of the cannulae (not including the threads 58, 60) range from 0.710 inches at the flared proximal end to 0.560 inches at the intermediate portion to 0.432 inches at the distal end. The threads 58, 60 are raised 0.045 inches from the non-threaded portions of the exterior surfaces 50, 52 of the cannulae 12, 18. The cannulae 12, 18 have overall lengths of 2.1 inches from the top surfaces 74, 76 of the flanges 38, 40 to the distal ends. The cannulae flanges 38, 40 have outer diameters of 1 inch. The obturator flanges 108, 110 also have outer diameters of 1 inch. The intermediate portions 112, 114 of the obturators 14, 20 have outer diameters of 0.409 inches. The intermediate portions 112, 114 and distal end portions 34, 36 have total lengths of 2.650 inches. Generally, the intermediate portion of each obturator is sized and shaped for slidable, substantially co-axial and removable movement in the central longitudinal channel of the respective cannula. It should be understood that all of these dimensions are provided as examples only; the present invention is not limited to any particular dimension unless expressly called for in the claims.

Figure 11:
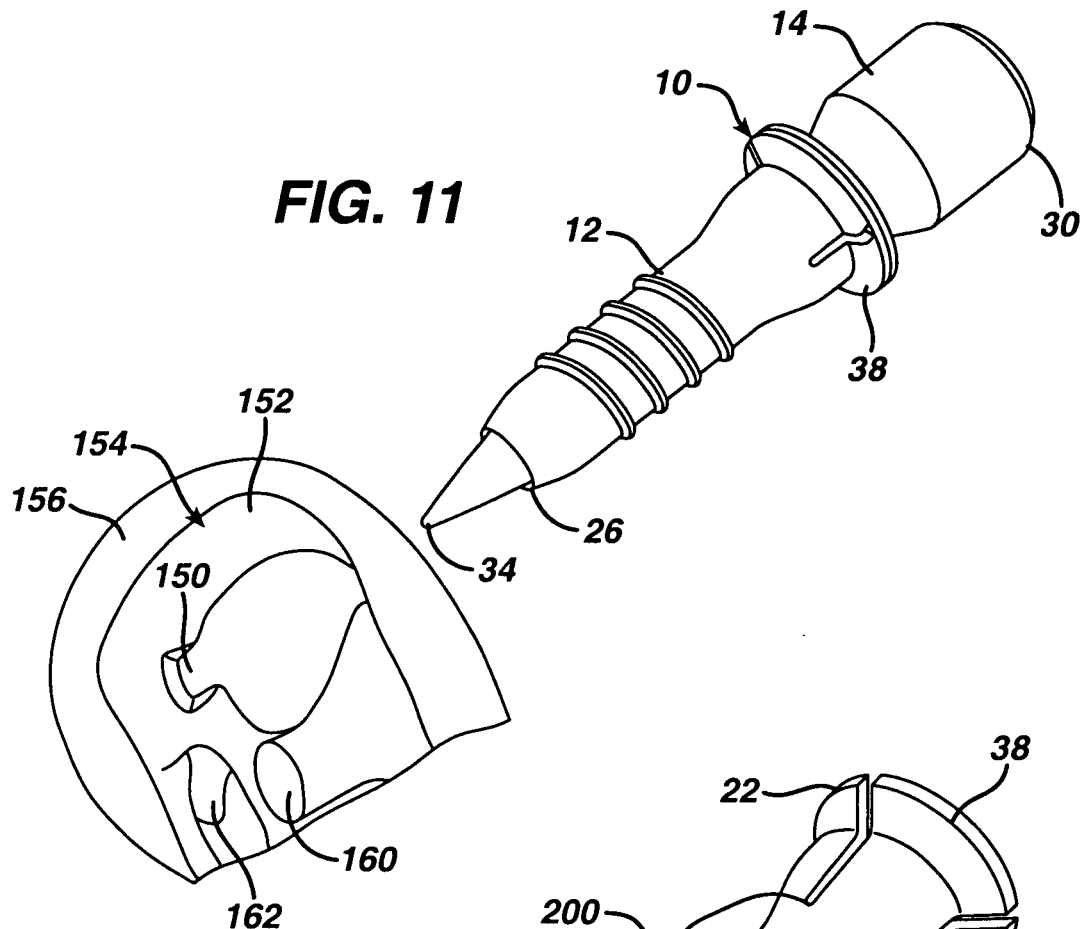
FIG. 11 is a perspective view of the instrument set of FIG. 1, shown in relation to a mensicus.
Figure 12:
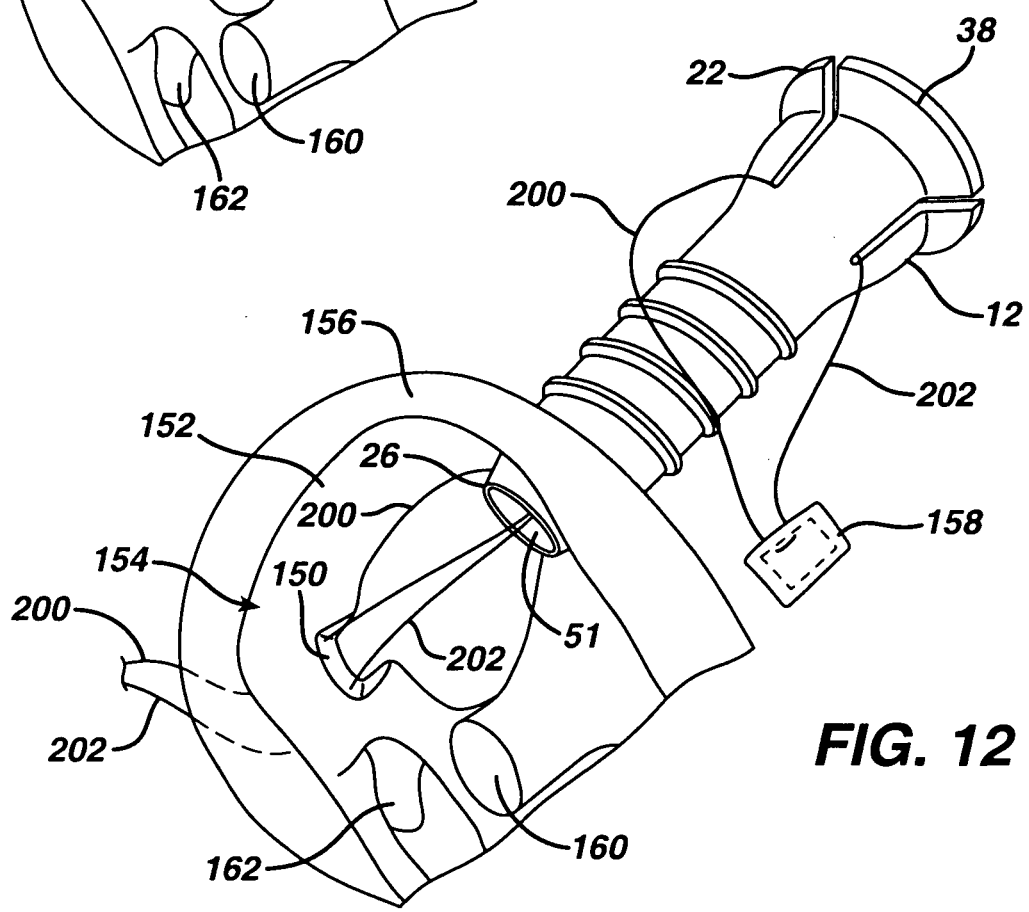
FIG. 12 is a perspective view of the cannula of FIGS. 1, 3 and 5-6, shown in use with a meniscus, a therapeutic implant and suture.
Figure 13:
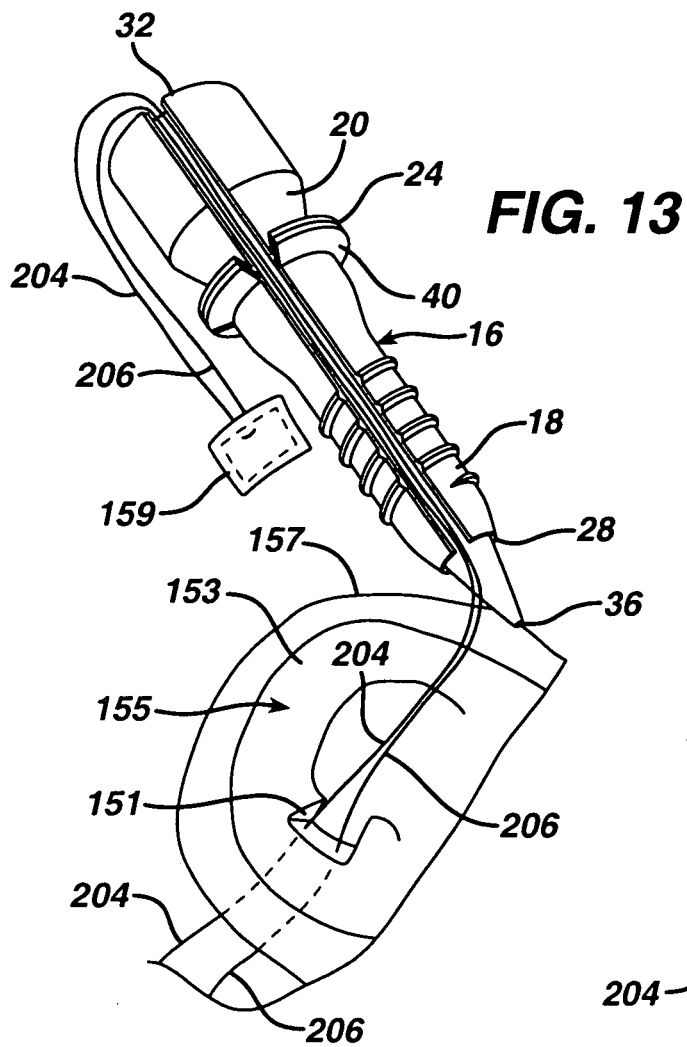
FIG. 13 is a perspective view of the instrument set of FIG. 2, shown in relation to a meniscus and to suture passed through the meniscus and through a therapeutic implant.
Figure 14:
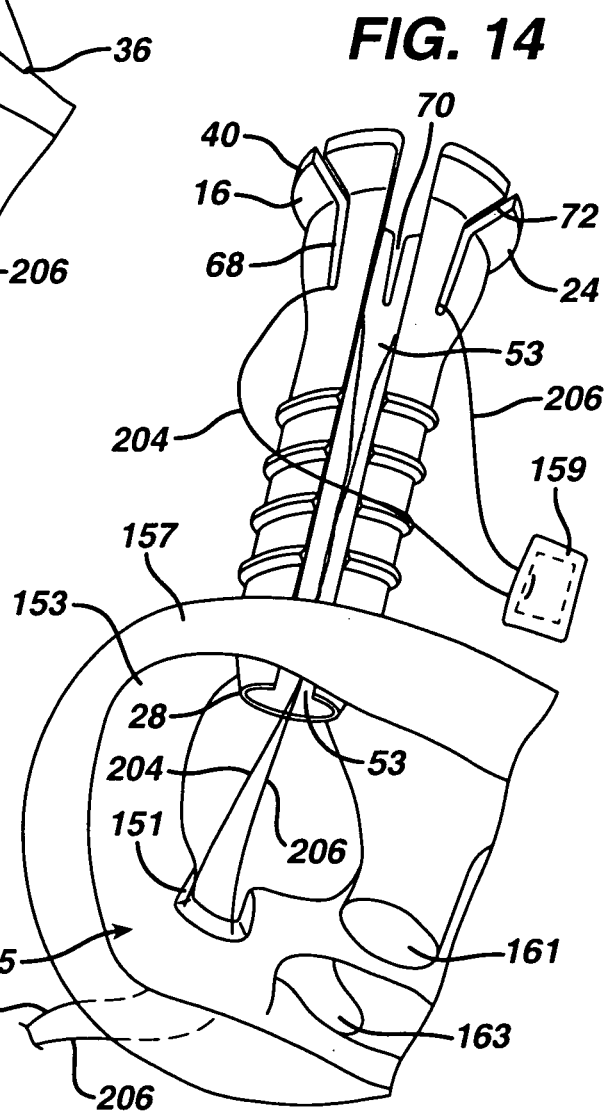
FIG. 14 is a perspective view of the cannula of FIGS. 2, 7 and 9-10 shown in use with a meniscus, a therapeutic implant and suture.

Use of the illustrated instrument sets or assemblies 10, 16 is described below and illustrated diagrammatically in FIGS. 11-14 in treating a defect 150, 151 in the meniscus 152, 153 in the knee joint space 154, 155. Patient tissue (including skin and subcutaneous tissue) surrounding the knee joint is illustrated diagrammatically in FIGS. 11-14 at 156, 157. Therapeutic implants are illustrated diagrammatically in FIGS. 12-14 at 158, 159. In FIGS. 11-12 and 14, a portion of the anterior cruciate ligament is shown at 160, 161 and a portion of the posterior cruciate ligament is shown at 162, 163.

In the illustrations, the tissue defect 150, 151 comprises a gap in the posterior portion of the medial horn of the meniscus 152, 153 created by a partial menisectomy. Although not described in detail below, it should be understood that the technique described below may also be used in treating tissue defects in other areas of the medial horn of the meniscus as well as in the lateral horn of the meniscus. It should also be understood that the technique described below may also be applied in treating defects at other tissue sites in a patient's body.

Figure 16:
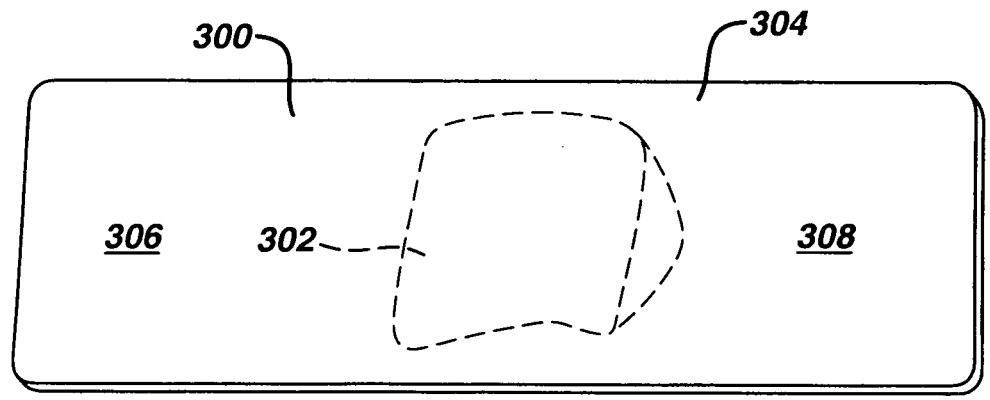
FIG. 16 is a perspective view of the superior side of a meniscal implant.
Figure 17:
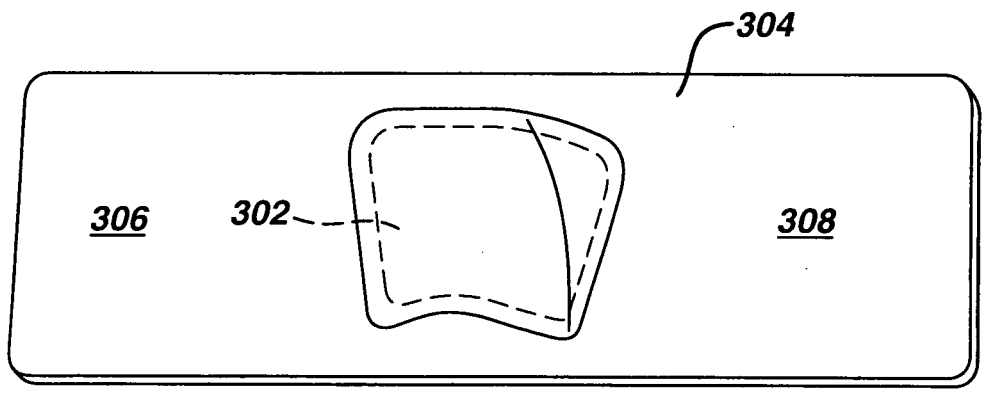
FIG. 17 is a perspective view of the inferior side of the meniscal implant of FIG. 16.
Figure 18:
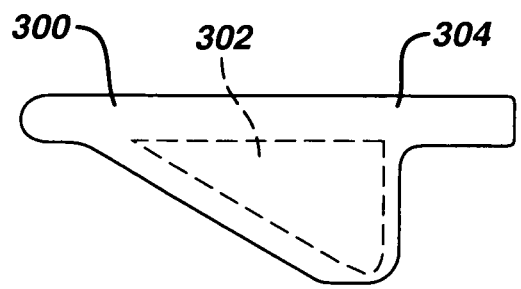
FIG. 18 is a side elevation of the meniscal implant of FIGS. 16-17.

Although the present invention is not limited to any particular type of therapeutic implant, the implant disclosed in U.S. patent application Ser. No. 10/747,349, entitled "Implantable Tissue Repair Device and Method," filed on Dec. 29, 2003 by Malaviya et al., which is incorporated by reference herein in its entirety, may be particularly useful. An example of a meniscal implant is illustrated at 200 in FIGS. 16-18. The implant 300 includes a wedge 302 of tissue regeneration material and a cover 304. The cover 304 may also be made of tissue regeneration material. The cover 304 may have side wings 306, 308. Depending on the defect site and the fixation sites, the surgeon may trim the side wings 306, 308 to a desired shape, or may trim off all or substantially all of the side wings 306, 308 to a desired configuration and used for fixating the implant.

The therapeutic implant, method of making the implant, and method of repairing cartilage using the implant may include the teachings of the following U.S. patent applications, the complete disclosures of which are incorporated by reference herein: Ser. No. 10/172,347 entitled "Hybrid Biologic-Synthetic Bioabsorbable Scaffolds" (U.S. Patent Publication No. 20030023316A1); Ser. No. 10/195,334 entitled "Cartilage Repair and Regeneration Scaffolds and Method" (U.S. Patent Publication No. 20030033021A1); Ser. No. 10/195,341 entitled "Hybrid Biologic/Synthetic Porous Extracellular Matrix Scaffolds" (U.S. Patent Publication No. 20030021827A1); Ser. No. 10/195,344 entitled "Unitary Surgical Device and Method" (U.S. Patent Publication No. 20030078617A1); Ser. No. 10/195,354 entitled "Porous Extracellular Matrix Scaffold and Method" (U.S. Patent Publication No. 20030044444A1); Ser. No. 10/195,606 entitled "Cartilage Repair and Regeneration Device and Method" (U.S. Patent Publication No. 20030033022A1); Ser. No. 10/195,633 entitled "Porous Delivery Scaffold and Method" (U.S. Patent Publication No. 2003-0049299A1); Ser. No. 10/195,719 entitled "Devices from Naturally Occurring Biologically Derived Materials" (U.S. Patent Publication No. 20030032961A1); and Ser. No. 10/195,794 entitled "Meniscus Regeneration Device and Method" (U.S. Patent Publication No. 20030036797A1). As disclosed in those patent applications, the implant may include naturally occurring extracellular material, a biocompatible polymer, a hybrid of materials, bioactive agents, biologically derived agents, cells, biological lubricants, and biocompatible inorganic materials, for example.

The surgeon can perform standard arthroscopic procedures to create portals to gain access to the joint space 154, 155. Standard arthroscopic scopes and probes may be used for inspection of the meniscus and surrounding tissue. The surgeon may prepare the site in a standard manner, clearing away the fat pad utilizing arthroscopic shavers, scissors and punches. The site for the location of the therapeutic implant 158, 159 may be prepared by removing loose tissue, trephinating the rim, rasping the synovium, and shaving off bone and cartilage from the condyle. Site preparation may include a partial meniscectomy, leaving a gap as illustrated in FIGS. 11-14 to receive a therapeutic implant.

After the site has been prepared, the defect may be sized and measured. Instruments such as those disclosed in the following U.S. patent applications, all filed concurrently herewith, may be used for sizing and measurement: U.S. Provisional Patent Application entitled "Implant System and Method With Sizing Templates," (Docket No. 5259) filed by Anthony D. Zannis, Danny E. McAdams, Brian A. Magee, Herbert E. Schwartz and Andrew M. Jacobs; United States Provisional Patent Application entitled "Coordinate Instrument Set," (Docket No. 5372) filed by Anthony D. Zannis, Herbert E. Schwartz, Prasanna Malaviya, Keith M. McGrath, Danny E. McAdams, Andrew M. Jacobs, Jack Farr, M. D. and Randall L. Holcomb, M. D. The complete disclosures of these patent applications are incorporated by reference herein.

The therapeutic implant 158, 159 may then be prepared for delivery to the joint space and fixation to native tissue.

Both the first and second illustrated sets or assemblies 10, 14 of instruments may be used as follows. First, the surgeon would assemble either the first cannula 12 and first obturator 14 or the second cannula 18 and second obturator 20 by inserting the distal end 34 or 36 of the obturator 14 or 20 into the proximal end 22 or 24 of the appropriate cannula 12 or 18. When assembled, the cannula/obturator combination (either elements 12 and 14 or elements 18 and 20) appear as shown in FIGS. 1, 2, 11 and 13: the bottom surfaces 78, 80 of the cannulae flanges 38, 40 are juxtaposed with the top surfaces 117, 119 of the obturator flanges 108, 110 and the distal tips 116, 118 of the obturators 14, 20 are exposed beyond the distal ends 26, 28 of the cannulae 12, 18. So assembled, the obturator pegs or projections 103, 104, 105, 106 are received in the mating radial recesses 99, 100, 101, 102 in the top surfaces 74, 76 of the cannulae flanges 38, 40 and relative rotation between the cannulae 12, 18 and obturators 14, 20 is prevented. In the second instrument set or assembly 16, the mating pegs 104, 106 and recesses 100, 102 also serve to align the cannula longitudinal through slot 94 with the obturator slot 124.

The surgeon may then place the assembly 10 or 16 into the insertion incision through the patient's surrounding tissue 156 or 157 and screw the assembly into the tissue until the distal end of the cannula 12 or 18 is in the joint space 154 or 155. The proximal ends of the assemblies 12 or 16 are exposed outside of the patient's body. The obturator 14 or 20 may then be retracted by pulling it in a proximal direction, leaving the cannula 12 or 18 in place. The threads 58 or 60 prevent the cannula 12 or 18 from releasing, creating a firm and secure pathway through the longitudinal passageway 51 or 53 from outside the patient's body to the joint space 154 or 155.

The surgeon may then place sutures or other fixating mechanisms through the therapeutic implant and pass the needles carrying the sutures through the longitudinal passageway 51 or 53, through native tissue at the defect site and out again through the patient's surrounding tissue 156 or 157. For each length of suture (shown at 200, 202, 204 and 206 in FIGS. 12 and 14), an exterior portion may be placed in one of the cannulae through slots 62, 64, 66, 68, 70, or 72 to keep the lengths of suture separate and distinct from one another and prevent entanglement. In addition, keeping the lengths of suture separate and visible from outside of the patient's body allows the surgeon to readily distinguish one from the other. The surgeon may then pull the suture lengths that have been passed through the patient's tissue to pull the therapeutic implant 158 or 159 from outside the patient's body distally into and through the longitudinal passageway 51 or 53 of the cannula 12 or 18 until the therapeutic implant is in place at the defect site 150 or 151. The sutures 200, 202 or 204, 206 may then be tied off to secure the implant in place. Additional needles and sutures may be passed through the cannula 12 or 18 to further fix the implant in place; these additional sutures may also be maintained separate by placing an exterior portion of each suture in one of the slots 62, 64, 66, 68, 70, 72. When the implant is completely fixed in place, the surgeon may then reintroduce the obturator 14 or 20 and then screw the assembly 10 or 16 out of the tissue.

The second assembly or set of instruments 14 has an additional functionality due to the presence of the aligned longitudinal slots 94, 124. As illustrated in FIG. 13, the second instrument assembly or set 14 can be used after sutures have already been introduced into the joint space. As there illustrated, the sutures 204, 206 may be pulled through the longitudinal slot 94 of the cannula 18 and into the longitudinal slot 124 of the obturator while the cannula/obturator assembly is outside of the patient's body. The cannula/obturator assembly 16, with the sutures in the slot 124, can then be inserted into the insertion incision through the patient's surrounding tissue 156 or 157 and screwed into the tissue until the distal end of the cannula 18 is in the joint space 155. The proximal end of the assembly 16 is exposed outside of the patient's body. The surgeon can then retract the obturator 20 by pulling it in a proximal direction and then separate the sutures 204, 206, placing an exterior portion of each suture 204, 206 in one of the slots 68, 70, 72 in the cannula 18. The surgery may then continue as described above. To deliver the implant through the cannulae 12 or 18, devices may be used like those disclosed in the following United States patent applications, which are incorporated by reference herein in their entireties: U.S. patent application Ser. No. 10/610,287 entitled "Slide and Kit for Delivering Implants" (filed Jun. 30, 2003) and U.S. Provisional Patent Application Ser. No. 60/483,804 entitled "Instrument for Delivery of Implant" (filed Jun. 30, 2003). However, the present invention is not limited to any particular implant, surgical technique or surgical instrument unless expressly set forth in the claims.

In addition, other surgical instruments, such as graspers, can be inserted through the channel of either of the illustrated cannulae 12 or 18 and used intra-operatively with the cannulae in place. The cannulae 18 of the second assembly or set of instruments 14 has an additional advantage due to the presence of the longitudinal slot 94: with the cannulae 18 in place as illustrated in FIG. 14, the cannulae 18 can be removed from the joint space without removing the instruments or suture connected to devices larger than the cannulae channel, since the instruments and suture can be passed through the longitudinal slot 94.

Other steps may be taken to facilitate suture management throughout the surgical procedure. For example, sutures of different colors could be used to assist the surgeon in distinguishing between sutures.

Although the technique of the present invention has been described above with respect to an arthroscopic procedure, it should be understood that the instruments and technique of the present invention can also be used with more invasive surgical procedures, such as a mini-arthrotomy or an open surgical procedure.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A surgical cannula kit comprising a cannula and an obturator:
    wherein the cannula includes a proximal end, a distal end and a central longitudinal axis, the cannula comprising an annular flange at the proximal end, the flange having a central opening, a top surface and a bottom surface, a body extending from the annular flange to the distal end of the cannula, the body including a proximal portion adjacent to the annular flange and an interior surface defining a central axial channel extending from the central opening of the annular flange to the distal end, the body being open at the distal end, the body further including an exterior surface and having raised threads extending outwardly from the exterior surface of the body between the annular flange and the distal end;
    wherein the cannula further comprises a pair of spaced surfaces defining a through slot extending radially across the entire flange and through the entire thickness of the flange, the through slot further extending distally through the proximal portion of the body from the exterior surface to the interior surface, the through slot terminating at a location distal to the bottom surface of the annular flange and proximal to the distal end of the cannula;
    wherein the cannula further comprises a pair of spaced surfaces defining a longitudinal slot extending through the flange, threads and body of the cannula from the proximal end to the distal end, the longitudinal slot providing a passageway between the longitudinal channel of the cannula and the exterior of the cannula along the entire length of the cannula;
    wherein the obturator includes a proximal portion, a distal portion terminating in a distal end, an intermediate portion and a flange between the intermediate portion and the proximal portion, the obturator being sized and shaped so that the intermediate portion is receivable and slidable in the central axial channel of the cannula; and
    wherein the obturator further comprises a pair of spaced surfaces defining a longitudinal slot in the distal portion, intermediate portion, flange and proximal portion.

2. The surgical cannula kit of claim 1 wherein the cannula further comprises a second pair of spaced surfaces defining a second through slot extending radially across the entire flange and through the entire thickness of the flange, the second through slot further extending distally through the proximal portion of the body from the exterior surface to the interior surface, the second through slot terminating at a location distal to the bottom surface of the annular flange and proximal to the distal end of the cannula, the second through slot being spaced from the first through slot.

3. The surgical cannula kit of claim 2 wherein the cannula further comprises a third pair of spaced surfaces defining a third through slot extending radially across the entire flange and through the entire thickness of the flange, the third through slot further extending distally through the proximal portion of the body from the exterior surface to the interior surface, the third through slot terminating at a location distal to the bottom surface of the annular flange and proximal to the distal end of the cannula, the third through slot being spaced from the first through slot and second through slot.

4. The surgical cannula kit of claim 1 wherein the longitudinal slot in the obturator extends the entire length of the obturator.

5. The surgical cannula kit of claim 1 wherein the obturator flange and cannula flange include mating anti-rotation members.

6. The surgical cannula kit of claim 5 wherein the longitudinal slot of the obturator and longitudinal slot of the cannula are aligned when the mating anti-rotation members are engaged.

7. The surgical cannula kit of claim 1 further comprising a therapeutic implant having characteristics suitable for implantation at a meniscal defect site.

8. The surgical cannula kit of claim 1 wherein the distal portion of the obturator comprises a distal tip having a frusto-conical shape.

9. The surgical cannula kit of claim 1 wherein the annular flange of the cannula and annular flange of the obturator includes engageable complementary structures to limit relative rotation between the cannula and obturator.

10. The surgical cannula kit of claim 9 wherein the complementary structures comprise mating pegs and recesses.

* * * * *